United States Patent [19]

Stein

[11] Patent Number: 5,044,002
[45] Date of Patent: * Aug. 27, 1991

[54] BAGGAGE INSPECTION AND THE LIKE

[75] Inventor: Jay A. Stein, Framingham, Mass.

[73] Assignee: Hologic, Inc., Waltham, Mass.

[ * ] Notice: The portion of the term of this patent subsequent to Mar. 7, 2006 has been disclaimed.

[21] Appl. No.: 320,156

[22] Filed: Mar. 7, 1989

Related U.S. Application Data

[63] Continuation-in-part of Ser. No. 78,419, Jul. 27, 1987, Pat. No. 4,811,373, which is a continuation-in-part of Ser. No. 885,098, Jul. 14, 1986.

[51] Int. Cl.$^5$ .................................... G01N 23/06
[52] U.S. Cl. ............................ 378/54; 378/57; 378/62; 378/158
[58] Field of Search ............... 378/51, 53, 54, 56, 378/57, 62–63, 69, 158, 99; 358/111

[56] References Cited

U.S. PATENT DOCUMENTS

| Re. 28,544 | 9/1975 | Stein et al. | 378/57 |
|---|---|---|---|
| 3,832,545 | 8/1974 | Bartko | 378/57 |
| 3,848,130 | 11/1974 | Macovski | 378/53 |
| 3,854,049 | 12/1974 | Mistretta et al. | 378/62 |
| 3,924,133 | 12/1975 | Reiss | 378/54 |
| 3,944,830 | 3/1976 | Dissing | 378/55 |
| 3,996,471 | 12/1976 | Fletcher et al. | 378/53 |
| 4,029,963 | 6/1977 | Alvarez et al. | 378/62 |
| 4,639,943 | 1/1987 | Heinze et al. | 378/96 |
| 4,641,331 | 2/1987 | Makino et al. | 378/108 |
| 4,799,247 | 1/1989 | Annis et al. | 378/57 |
| 4,811,373 | 3/1989 | Stein | 378/54 |
| 4,839,913 | 6/1989 | Annis et al. | 378/99 |

OTHER PUBLICATIONS

Lehmann et al., *Generalized Image Combinations in Dual KVE Digital Radiography*, Medical Physics, vol. 8, No. 5, p. 659, Sep./Oct. 1981.
Sartoris et al., *Bone Mineral Density in the Femoral Neck*, American Journal of Roentgenology, vol. 144, p. 605 (1985).
Gustafsson et al., *X-Ray Spectrophotometry for Bone–Mineral Determinations*, Medical and Biomedical Engineering, p. 113, (Jan. 1974).
Cann, *A Clinicians Guide to the Use of Bone Mass Measurements*, University of Califormia, pp. 1–36 (unpublished).
Wahner et al., *Non-Invasive Bone Mineral Measurements*, Seminars in Nuclear Medicine, vol. XIII, No. 3, p. 282, Jul., 1983.
Dunn et al., *Measurement of Bone Mineral Content in Human Vertebrae and Hip by Dual Proton Absorptiometry*, Radiology, vol. 136, No. 2, p. 485 (Aug., 1980).
The "Norland Dichromatic Bone Densitometer", pamphlet.
The Boston Globe, "U.S. says American Airlines has poor security record", Feb. 18, 1989.

*Primary Examiner*—Janice A. Howell
*Assistant Examiner*—John C. Freeman
*Attorney, Agent, or Firm*—Fish & Richardson

[57] ABSTRACT

Apparatus for inspecting baggage moved relative to an x-ray beam. The apparatus causes a beam of x-rays to pass through a reference in the course of exposure and detects the presence of the reference material contained within the baggage by matching the effective atomic number of the materials within the bag, with the atomic number of the reference.

3 Claims, 6 Drawing Sheets

BAGGAGE INSPECTION AND THE LIKE

This application is a continuation-in-part of U.S. Pat. application Ser. No. 078,419 filed July 27, 1987, now issued as U.S. Pat. No. 4,811,373, which is a continuation-in-part of U.S. Pat. application Ser. No. 885,098, filed July 14, 1986, both of which are herein incorporated by reference.

BACKGROUND OF THE INVENTION

This invention is related to the field of x-ray baggage inspection.

It also provides improvements that may be useful in the general field of determining the presence of known substances within bodies of interest.

The invention provides x-ray absorptiometer techniques suitable to respond to the effective atomic number of objects located within baggage to indicate objects having a given composition. Such measurements are useful to help detect prohibited substances such as explosives or narcotics concealed in baggage. To be effective, such an apparatus must, within practical cost constraints, satisfy many criteria related e.g. to measurement time, resolution, accuracy, precision, and minimization of radiation exposure. Prior efforts to use x-ray sources to detect prohibited substances have not been altogether successful, or have had drawbacks.

SUMMARY OF INVENTION

The invention can employ an x-ray tube past which the baggage to be inspected is moved. The x-ray tube may have a fixed relationship with a collimator to produce a fan beam aligned with a detector or a scanner can sweep a pencil beam across the object and the detector. In either case alternating high and low voltage levels are applied to the x-ray tube or other provisions are made for effecting a dual energy scan. At the same time a reference material is moved in and out of the beam. Signal processing of the signals based effectively on four images respectively with high and low-energy beams and with and without the selected reference material can produce from the signals an indication whether or not a substance similar to the reference material is present in the baggage.

According to one aspect of the invention, an apparatus is provided for responding to the absorption characteristic of material in a piece of baggage which is moved relative to an x-ray beam. The apparatus includes an x-ray tube means having a power supply, and detector means arranged to detect x-rays attenuated by the baggage on the basis of a dual energy scan. The apparatus also comprises means for causing the beam to pass through a reference material in the course of the exposure, and signal processing means responsive to the output of the detector means to provide an indication of presence of the target substance, which may be a representation of the profile of the suspect object within the baggage (e.g., an x-ray film-like picture of the baggage) indicating the object contained within the baggage distribution which matches the effective atomic number of the material sought, the signal processing means adapted to respond to data based upon x-rays attenuated by the reference material.

In preferred embodiments of these aspects of the invention, the power supply of the apparatus is adapted to apply alternate high and low voltage levels to the x-ray tube; control means for the frequency of the voltage is related to the speed at which the baggage passes between the x-ray tube, and the detector means and the beam thickness, produced by the collimator, to apply alternating high and low voltage levels to the x-ray tube at a frequency sufficiently high that at least one pair of high and low level exposures occurs during the short time period during which the fan beam traverses a distance equal to about one beam thickness, preferably the apparatus is being adapted to produce pairs of high and low voltage pulses at a rate of the order of sixty per second, the baggage being driven along at a rate of the order of six inches per second and the collimator produces a fan beam of between about one and three millimeters in thickness; the x-ray beam passes through the reference material at least once per scan position for a period equal or less than the time during which one line of resolution is traversed, preferably the x-ray beam passes through the reference material for the duration of every other high and low voltage pulse pair; the detector means comprises an integrating detector controlled to integrate the detected signal repeatedly over time periods less than or equal to the time required to advance the x-ray scan pattern by one line of resolution, preferably an analog to digital converter being provided to convert each integrated value to a digital signal and a digital computer means is provided for producing the representation of the object within the baggage by processing the stream of the digital signals.

The present invention makes it possible to perform absorption measurements and detect objects in baggage more rapidly and with better resolution and accuracy than prior devices and so make suitable their use for baggage inspection.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

FIG. 1a is a digrammatic illustration of the preferred embodiment utilizing a fan beam, while

FIG. 2 is a plan view of the reference disc employed in the preferred embodiment with a fan beam, while

DESCRIPTION OF AN ILLUSTRATIVE EMBODIMENT

Figure 1A:
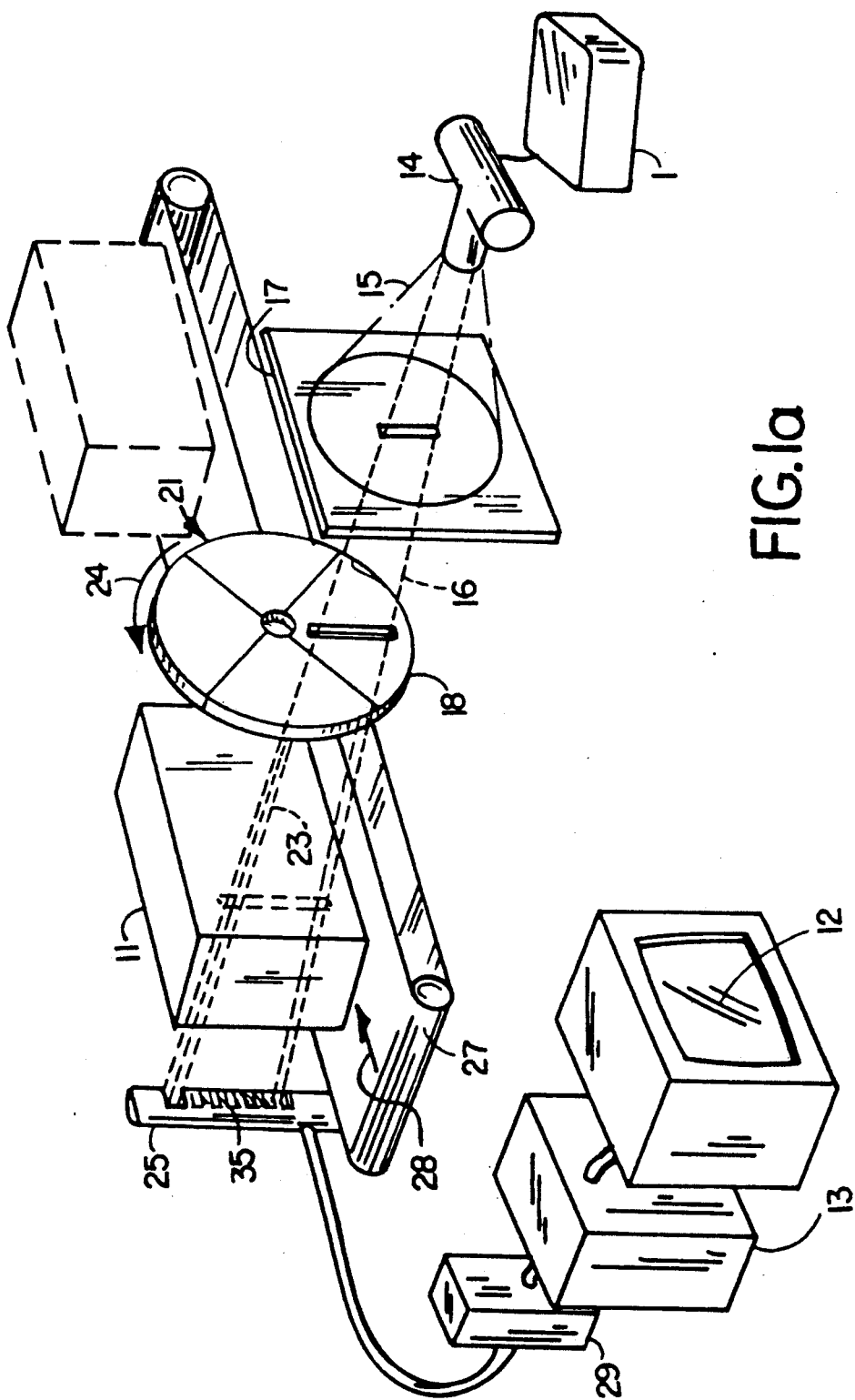
Figure 1C:
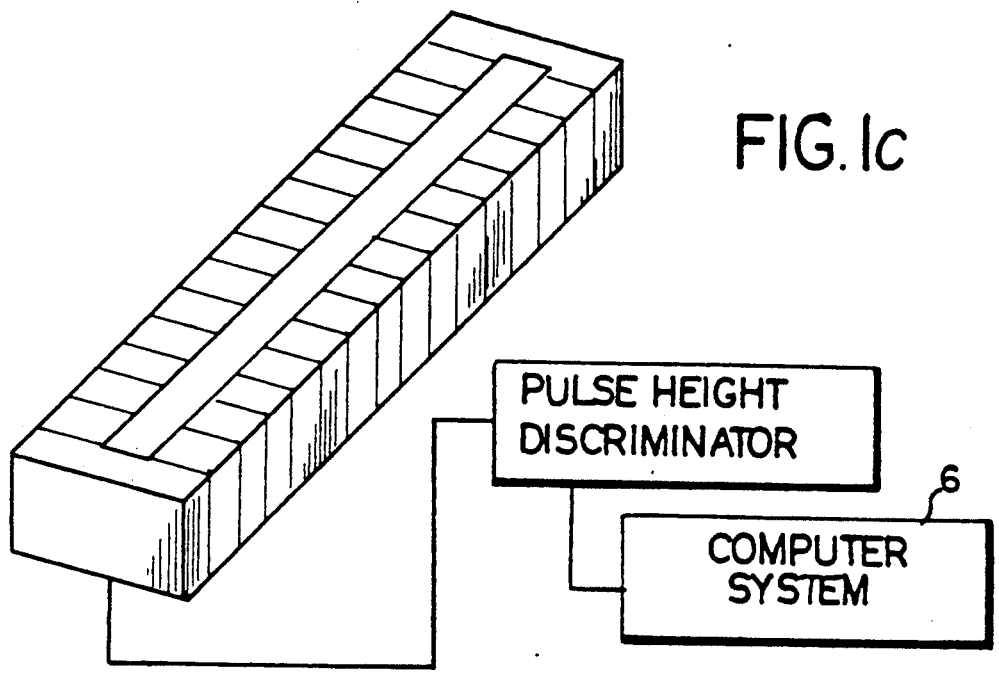
FIG. 1c illustrates an alternative using pulse height analysis.

Referring to FIG. 1a, a source of x-ray radiation 14 energized by a high voltage power supply 1 produces x-rays which pass through and are formed into a fan beam 16 by a slit collimator 17. The radiation is transmitted through a rotating (arrow 24) reference wheel 21 and the baggage to be inspected 11, to impinge on an array of x-ray detectors 25. The array of detectors 25 typically consists of a linear array of 500 to 1000 silicon photodiodes 35 located over 24 inches, which are covered with either an x-ray scintillation screen or an x-ray scintillation crystal. The screen or crystal produces light when struck by x-rays and the light is detected by the photodiodes 35 which produce electrical signals 26. These signals 26 are the input signals for an analog to digital (A/D) converter 29. The digital output of the A/D 29 converter is stored in a computer system 13 for further processing. An image signal is displayed on display device 12. The baggage 11 passes between the x-ray source 14 and detector array 25 on a conveyor belt 27 which moves in the direction of the arrow 28.

Considering the components in detail, the x-ray source is typically an x-ray tube having a cathode and an anode. Electrons are accelerated by the voltage between the anode and cathode and strike the anode. The anode is typically made of tungsten and the collision of electrons with the anode results in the emission of x-radiation from the point of collision with the anode, called the focal spot.

Figure 2:
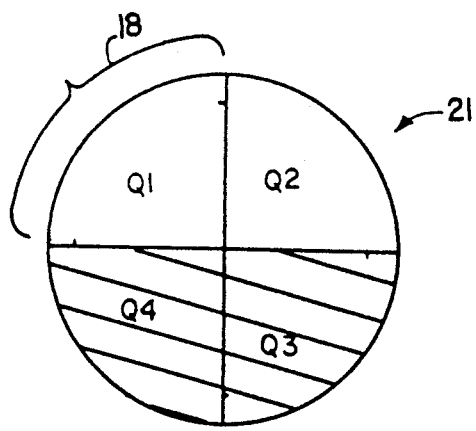

After being emitted by the x-ray tube, the x-rays from the anode which radiate as a broad pattern 15, are interrupted by the slit collimator 17 and turned into a fan beam 23. The slit collimator 17 is made of an x-ray opaque material such as lead or tungsten in which a rectangular slot has been machined. Thus the radiation passing through the slot in the collimator 17 forms a fan shape in space. Referring also to FIG. 2, the x-ray beam then passes through the reference wheel 21 consisting of a number of sectors 18. The longitudinal dimensions of the slot in the collimator is aligned with a radius of the wheel. Referring to FIG. 2, in one embodiment there are four sectors 18, labeled Q1 through Q4. Q3 and Q4 contain reference material corresponding to a substance sought to be detected. As the wheel 21 rotates, the x-ray beam passes through each of the quadrants 18 of the wheel 21 sequentially. Although the discussion to follow will be premised on a four sector reference wheel 21, there is no reason why a larger number of segments might not be used e.g. to inspect for more than one substance or to improve the detectability of a given substance.

Also, other means, besides the reference wheel 21 can be used to insert and remove the reference material. For example a solenoid could be used to insert and remove reference material into and from the beam. It should be noted that the reference wheel 21 can be located between the x-ray source 14 and the collimator or any where else in the beam line.

The reference wheel 21 is used in conjunction with a dual-energy x-ray technique wherein the x-ray scan of the object takes place at two energies. There are several methods for effectively conducting a dual-energy scan.

Figure 3:
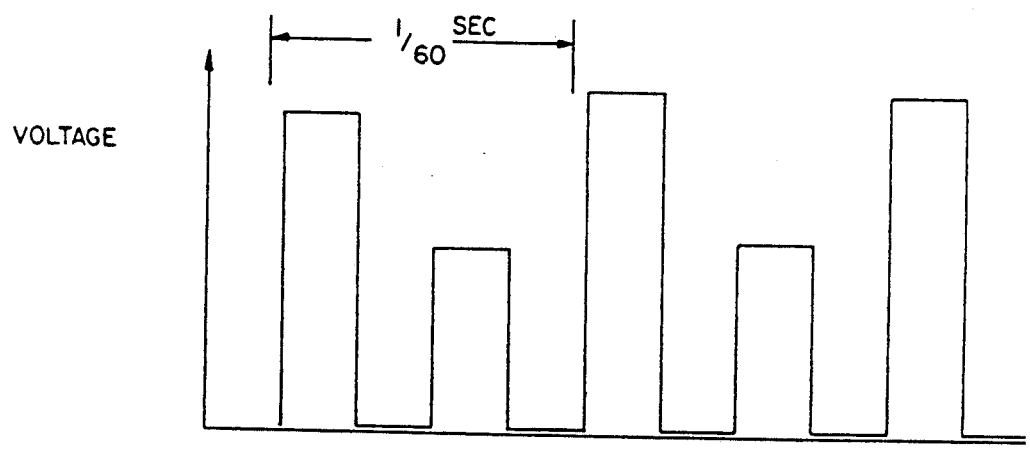
FIG. 3 is an illustration showing the time relationship between the voltage levels produced during the high energy level (HEL) and low energy level (LEL) phases of energization of the x-ray tube and the motion of the synchronized reference wheel having "reference material" and "no reference material" quadrants.

In one embodiment, the x-ray source 14 is an x-ray tube being operated in a pulsed manner. By operating the tube at alternately high- and low- kilovoltages, the x-ray radiation produced consists of an alternating series of high energy and lower energy x-ray pulses. In one embodiment the high energy pulses are produced at 150 kilovolts and the low energy pulses at 75 kilovolts. The tube current is typically between 0.5 and 6 milliamps for the array detector. The pulses so generated are spaced such that the time between the start of one pulse and the start of the adjacent pulse of different energy is 1/120 of a second. FIG. 3 depicts the time series of high energy (HEL) and low energy (LEL) pulses. Note that the time between adjacent pulses of the same energy is 1/60 sec.

Figure 4:
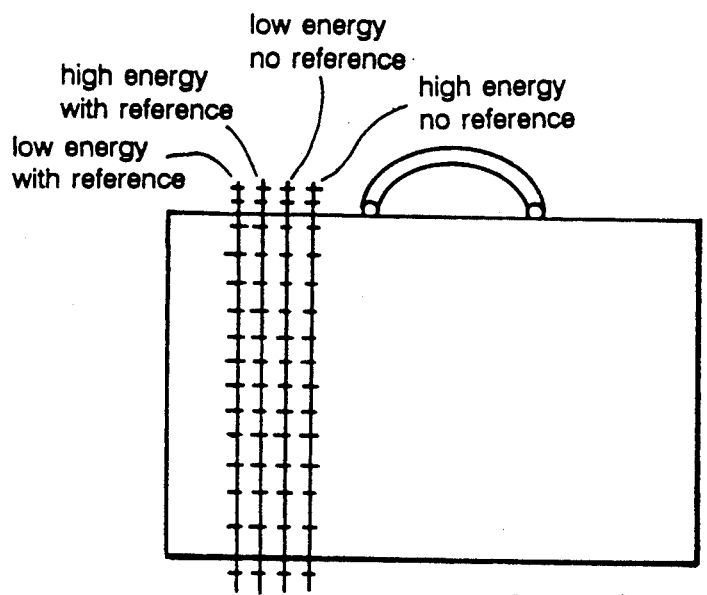
FIG. 4 represents a piece of baggage with superimposed scan pattern.

This dual energy beam is used in conjuction with the reference wheel 21 in the following manner. The first quadrant of the wheel 21 FIG. 2 lableed Q1 corresponds to a high energy pulse. The second quadrant labeled Q2 corresponds to a low energy pulse. Q3 corresponds again to a high energy pulse but with reference material in the path of the beam, while Q4 corresponds to a low energy pulse, also with reference material in the path of the beam. The pulses and the reference wheel sectors 18 are synchronized such that there are sequential scans of the baggage 11 occuring with high energy x-rays, low-energy x-rays, high-energy reference-attenuated x-rays and low-energy reference-attenuated x-rays as shown in FIG. 4. The values from each individual scan are stored such that they effectively provide four individual images of the contents of the baggage. That is, there will be one image made up of the scans that were done with high-energy beam, one image from the low-energy beam scans, one image from the high-energy beam scans through the reference material and one image from the low-energy beam scan through the reference material. The scan lines are actually much closer than shown in FIG. 4. There are typically at least four scan lines such as shown in FIG. 4 every 1 or 2 mm of scan distance.

Figure 2A:
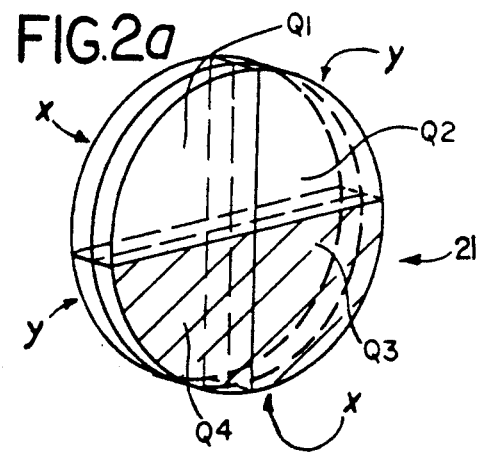
FIG. 2a illustrates an alternative which combines filtering material with the reference wheel.

Referring to FIG. 2a it is possible to include different filtering materials in the quadrants that also correspond to the high and low energy pulse to shape the spectrum of the energy present in the beam. Indeed, a second embodiment forms the dual energy beam by using a filtering technique instead of variation of voltage on the x-ray source. In this embodiment, the x-ray tube 14 is operated at constant voltage. Referring to FIG. 2a, different, selected materials x, y are provided in the wheel 21 to filter the x-ray beam differently and alternately so that during passage of one sector 18 of the wheel 21, the emerging beam contains a concentration of high-energy photons while during the next sector the emerging beam has a concentration of low-energy photons.

This is possible since a typical source generates a spectrum of x-rays and filtering materials can be selected to allow the passage through the material of either differentially more of the high-energy x-rays or more of the low-energy x-rays. In order to allow more of the low energy x-rays to pass through, K-edge filtering can be used. K-edge filtering makes use of the property of materials called the K-absorption edge. The K-absorption edge absorbs high energy photons preferentially over photons that have that have energy below this K-edge. Some rare earth materials such as gadolinium or sumarium have a K-edge in the neighborhood of 40 to 50 kilovolts and may be suitable for this purpose.

Figure 1B:
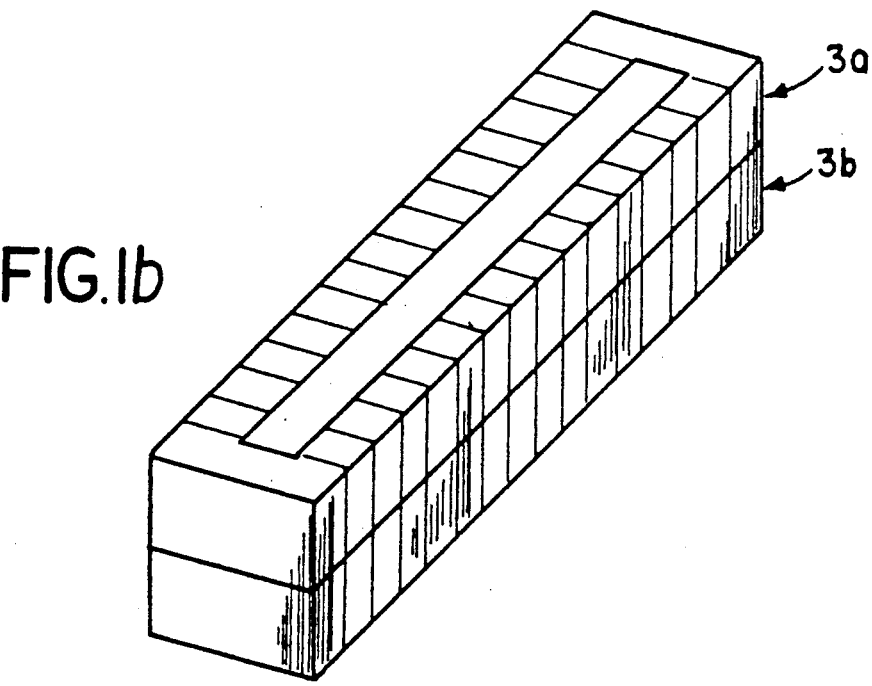
FIG. 1b illustrates an alternative using a sandwich detector.

Another embodiment of the invention obtains dual-energy scan with an unmodulated beam using a sandwich detector FIG. 1b. in which each detector element consists of a sandwich of two detectors 3a and 3b. Detector 3a which first receives the radiation tends to absorb the low-energy x-rays, while the detector 3b behind the first detector tends to absorb the high-energy x-rays which penetrate the first detector. Such a sandwich detector using different scintillation materials is well known in the art.

Figure 6:
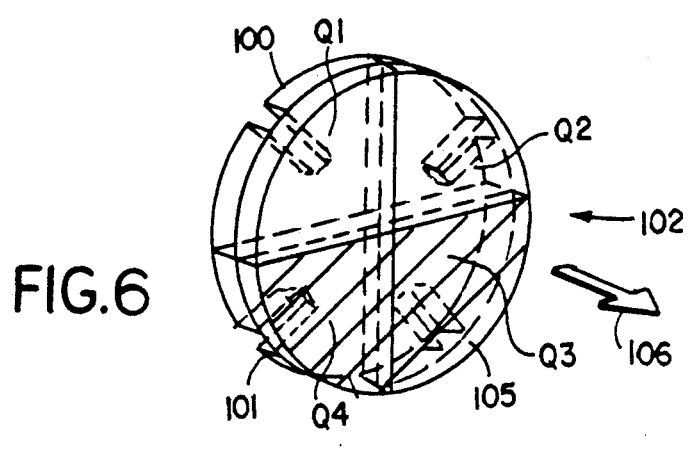
FIG. 6 represents an alternative reference disc to be used with a pencil beam.
Figure 5:
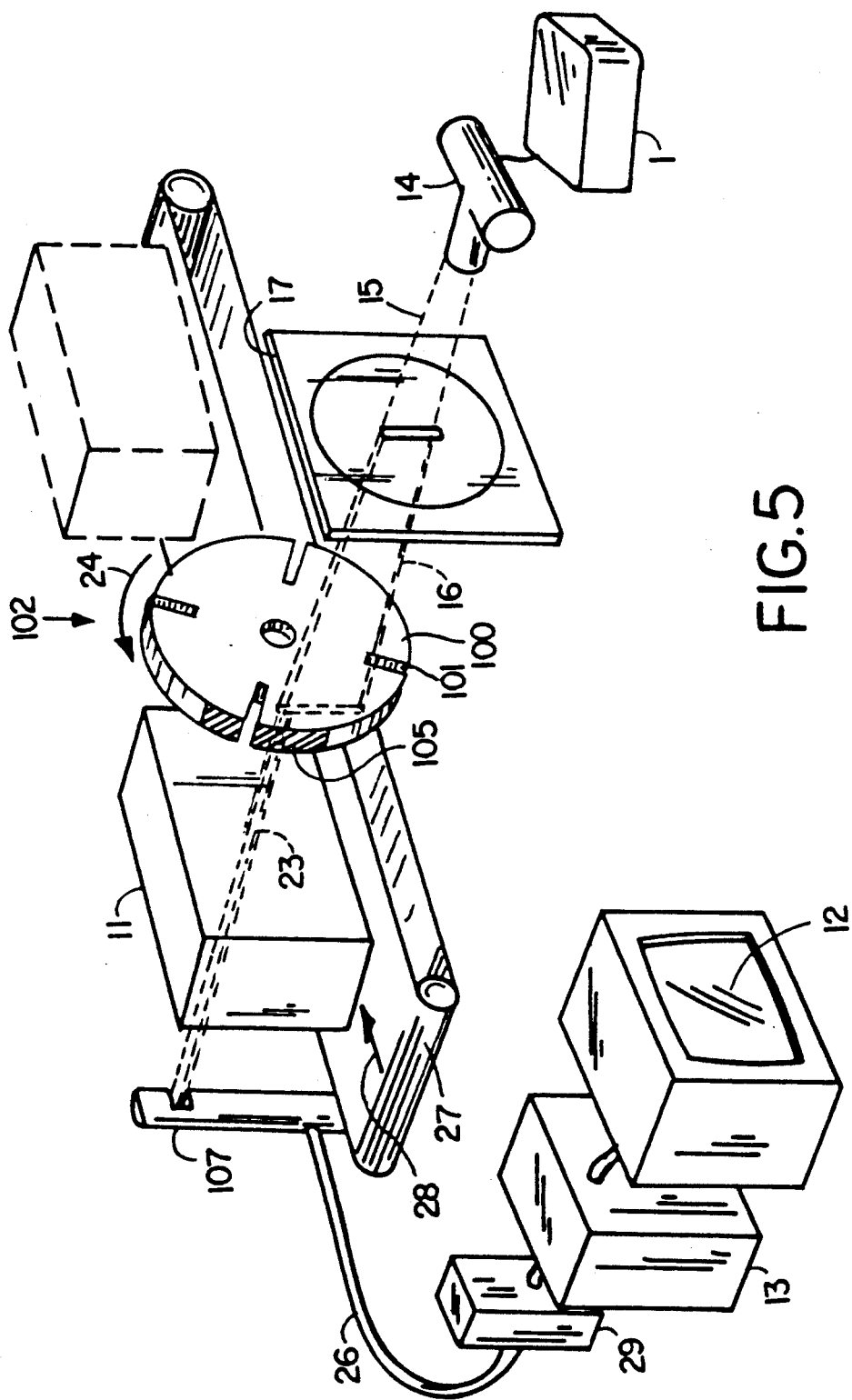
FIG. 5 represents an embodiment using a pencil beam.

Still another embodiment of the invention is shown in FIG. 5. In this embodiment a pencil beam 23 is formed by rotating 24 a dual purpose wheel 102 located in the path of the fan beam 16, with the vertically arranged fan beam aligned to impinge on an area of the wheel near the periphery at one side. The fan beam 16 is formed by the passing of x-rays 15 from a source 14 through a slit collimator 17. The first layer 100 of the wheel 102 is radio-opaque and stops the fan beam 16 except where slots 101 have been cut into the periphery of the wheel 102. As the slot 101 passes through the fan beam the intersection produces a pencil beam 23 which moves down the object 11 as the wheel 102 rotates. The pencil beam 23 penetrates the object 11 and impinges on the line-shaped detector 107. The rotation of the wheel 102 produces the vertical motion of the beam while the conveyor belt 27 moves the object 11 in the direction of the arrow 28 to produce the horizontal scan motion. Referring also to FIG. 6, the second disc in the dual wheel 102 is a disc having four sectors. The second disc is rigidly attached to the radiopaque disc and the two rotate together. The second disc can be the embodiments shown in FIG. 2 and 2a. Two adjacent sectors have the reference material so that when the pencil beam 23 is formed, some slots 101 produce a pencil beam 24 which passes through the reference material 105 in the direction shown by arrow 106, prior to striking the object to be scanned. In this way, the rotating wheel 102 both creates the pencil beam 23 and provides the reference material 105 to the high and low-energy beams. It should be noted that the dual energy x-ray beam can be created using all the previously described embodiments. In the embodiments just described, the sandwich detector is a single detector comprising two line shaped detectors located one above the other and the pulse height detector is a single line shaped detector connected to a pulse height discriminator.

Figure 7:
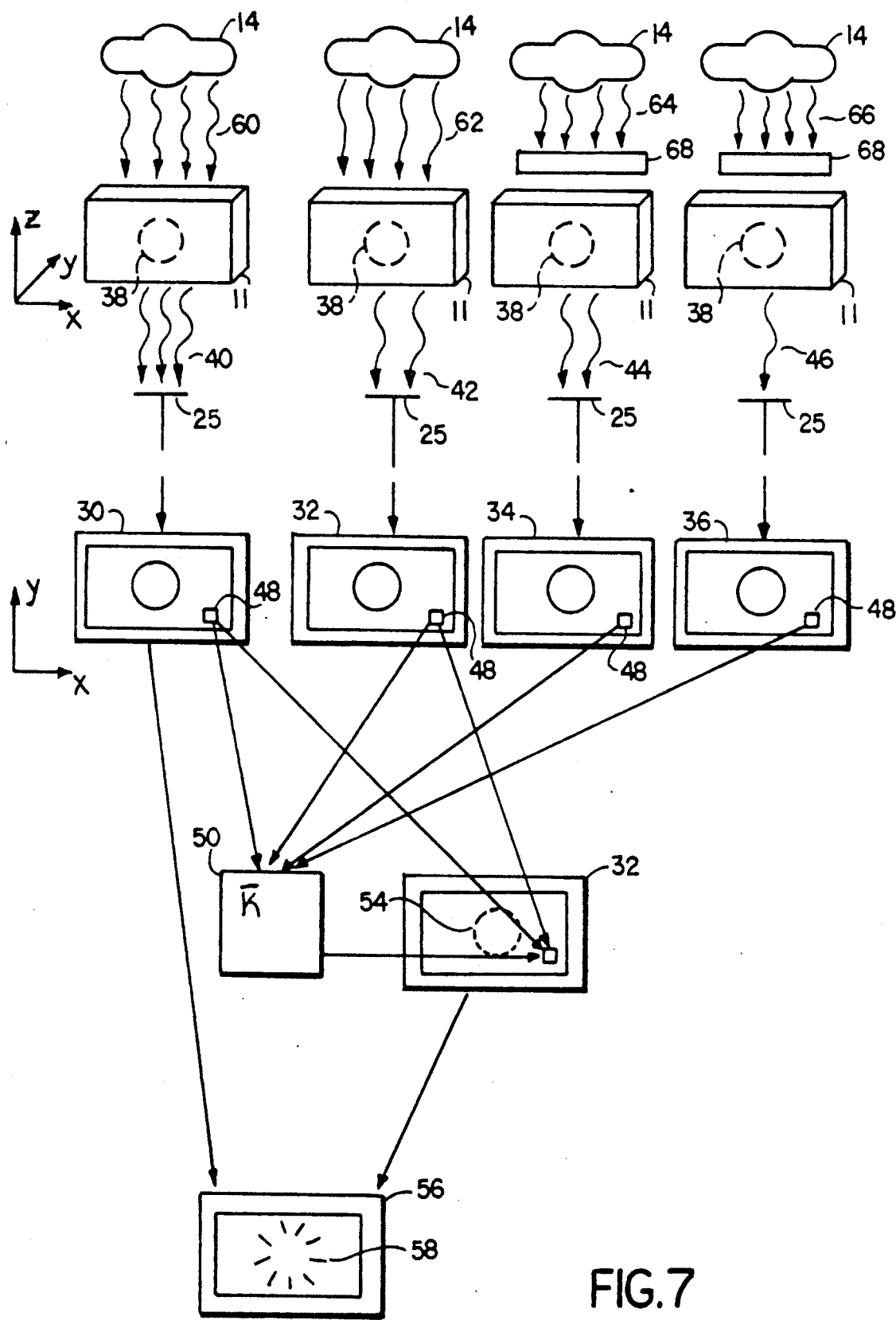
FIG. 7 is a diagram illustrating the operation of the embodiments that have been described.

The processing of the data collected preferably consists of performing mathematical operations on each of the picture elements (pixels) in each of the images taken of the baggage. Each image consists of an array of numbers which were obtained by converting the analog detector signal to digital values using the A/D converter 29. Referring to FIG. 7, the process by which the baggage is inspected is shown in diagramatic form. The baggage to be inspected 11 is exposed to a source of x-rays 14 producing, at different times, high-energy x-rays 60 and low-energy x-rays 62. Assume that the baggage 11 contains some contraband 38 of effective atomic number (Z).

The baggage 11 is first exposed to a high-energy x-ray beam 60 and the x-rays 40 which pass through the baggage 11 impinge on the detector 25 are digitized and effectively form a high-energy x-ray image 30. The baggage 11 is then exposed to a low-energy x-ray beam 62 and again, the x-rays 42 which pass through the baggage 11 form effectively a low-energy x-ray image 32. The high and low energy x-ray exposures are repeated with a reference material 68, also with an effective atomic number (Z), placed in the incident beam. Using high-energy 64 and low-energy 66 x-rays and the reference material 68 two additional images, a high-energy reference image 34 and a low-energy reference image 36 effectively are formed. It is not necessary to have complete images of the baggage before beginning the processing described. Ideally the processing takes place in parallel with the x-ray scanning so that at completion of the scanning the processing is complete.

For each picture element location 48, a value k is calculated 50 based upon the values from those four images. Where k is given by:

$$k = (L_c - L)/(H_c - H)$$

$L_c$ is the logarithm of the value of the pixel at the location of interest in the low-energy reference image, $H_c$ is the logarithm of the value of the pixel at the same coordinates in the high-energy reference image, L is the logarithm of the value of the pixel of the same coordinates in the low-energy image taken without the reference material and H is the logarithm of the value of the pixel at the same coordinate in the high-energy image also without the reference material.

It is possible to reduce the noise in k by averaging the k value, denoted by $\bar{k}$, by convolving k with a windowing function W such that:

$$\bar{k} = k * W$$

where * denotes convolution. The average is taken over a region of about between 3 and 50 pixels surrounding the pixel of interest. k is the ratio of the attenuation coefficients at low- and high-energy and is therefore is approximately independent of thickness. k depends only on the effective atomic number (Z) of the reference material.

$\bar{k}$ is used to form a new function Q which is also calculated at each pixel location and has the form $$Q = L - \bar{k} H.$$

Q forms a two dimensional array which is a new image 32 but an image in which an object which has the same effective atomic number Z as the reference material 68 is missing 54.

To understand why the object disappears from the image consider the following.

Assume that baggage is scanned and a Q image is calculated. Call this Q image $Q_1$ which has values given by $L_1 - \bar{k} H_1$. Next assume that an object with the same effective atomic number as the reference material is placed in the baggage and the baggage is scanned once more and a new Q image, $Q_2$, is formed, where $Q_2 = L_2 - \bar{k} H_2$. The two Q images differ by:

$$\Delta Q = Q_2 - Q_1 = (L_2 - L_1) - \bar{k}(H_2 - H_1)$$

Because of the way k is defined, at any location where the object added to the baggage has the same atomic number as the reference material, $\Delta Q = 0$. Therefore at these locations the pixel value will be the same as the value of $Q_1$. The object with the same effective atomic number as the reference material will not be seen. If the effective atomic number of the reference material and the object are close but not equal, the object will appear dimly compared to the background. By flashing on the screen the standard x-ray picture of the baggage and the Q image sequentially, the material with the same effective atomic number as the reference material will appear to blink. Thus, if the reference is contraband material, contraband material will stand out in the image and be recognizable by the operator. Other means of displaying the x-ray images may be contemplated including, for example, displaying the standard x-ray image and the Q image side by side; thereby relying on the operator to notice the difference.

It should be apparent that many types of reference material can be incorporated into a single wheel and a series of images can then be generated each selecting out various types of materials.

The disclosure of a U.S. patent application entitled Apparatus and Method for Analysis Using X-rays, also a Continuation-in-Part of U.S. Ser. No. 078,419, being filed simultaneously with this application, is herein incorporated by reference.

Having shown a number of embodiments, those skilled in the art will realize many variations are possible which will still be within the scope and spirit of the claimed invention. Therefore, it is the intention to limit the invention only as indicated by the scope of the claims.

What is claimed is:

1. An x-ray inspection apparatus comprising an x-ray tube means and associated power supply which generates an x-ray beam having a plurality of energies, means to expose to the x-ray beam an object to be inspected, means to insert into and remove from the x-ray beam a piece of reference material selected to have an absorption coefficient related to that of a substance the presence of which is to be detected, said means to insert and remove constructed to enable all regions of the object to be exposed both to the x-ray beam and to the beam obstructed by the reference material, detector means arranged on the opposite side of the object to detect x-rays and produce signals corresponding to the amount of x-rays transmitted through the object of each of a first and a second energy in the presence of said reference material and at each of said first and second energies in the absence of said reference material, and signal processing means responsive to signals from the detector means to produce an indication of the presence in the object of said substance based upon the signals produced by the exposure to the x-ray beams at each of said first and second energies in the absence of said reference material and the signals produced by the exposure to the x-ray beams at each of said first and second energies obstructed by the reference material of predetermined properties.

2. The apparatus of claim 1 for efficiently examining the object at more than one level of x-ray energy, said means to insert into and remove reference material acting upon beams of each level of x-ray energy.

3. The apparatus of claim 1 or 2 wherein said reference material is selected to have an absorption coefficient approximately equal to that of an explosive.

* * * * *